United States Patent
Cabello

(10) Patent No.: US 12,254,539 B2
(45) Date of Patent: Mar. 18, 2025

(54) SYSTEMS AND METHODS OF GUIDED PET RECONSTRUCTION WITH ADAPTIVE PRIOR STRENGTH

(71) Applicant: Siemens Medical Solutions USA, Inc., Malvern, PA (US)

(72) Inventor: Jorge Cabello, Lenoir City, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 365 days.

(21) Appl. No.: 17/930,565

(22) Filed: Sep. 8, 2022

(65) Prior Publication Data
US 2024/0095979 A1    Mar. 21, 2024

(51) Int. Cl.
*G06T 11/00* (2006.01)
*A61B 6/00* (2024.01)
*A61B 6/03* (2006.01)

(52) U.S. Cl.
CPC ........... *G06T 11/008* (2013.01); *A61B 6/037* (2013.01); *A61B 6/4417* (2013.01); *G06T 2210/41* (2013.01); *G06T 2211/424* (2013.01)

(58) Field of Classification Search
CPC ............... G06T 11/008; G06T 2210/41; G06T 2211/424; G06T 11/006; G06T 5/50; G06T 7/30; G06T 2207/10088; G06T 2207/10104; G06T 2207/20004; G06T 2207/20076; A61B 6/037; A61B 6/4417; A61B 6/5205; A61B 6/5247
See application file for complete search history.

(56) References Cited

U.S. PATENT DOCUMENTS

| | | | |
|---|---|---|---|
| 2010/0204563 A1* | 8/2010 | Stodilka | A61B 5/055 600/411 |
| 2014/0270448 A1* | 9/2014 | Mok | A61B 6/5264 600/538 |
| 2016/0055658 A1* | 2/2016 | Liang | G06T 11/006 382/131 |
| 2019/0043226 A1* | 2/2019 | Li | G06T 5/50 |
| 2023/0045406 A1* | 2/2023 | Zhang | G06T 5/50 |

OTHER PUBLICATIONS

Munoz, Camila, et al. "MRI-Guided Motion-Corrected PET Image Reconstruction for Cardiac PET/MRI." Journal of Nuclear Medicine 62.12 (2021): 1768-1774. (Year: 2021).*

(Continued)

*Primary Examiner* — Andrae S Allison

(57) ABSTRACT

Systems and methods of image reconstruction are disclosed. A positron emission tomography (PET) dataset is acquired from a PET imaging modality and a magnetic resonance imaging (MRI) dataset is obtained from an MRI modality. The MRI dataset is registered to the PET dataset. An MRI reconstructed image is generated from the MRI dataset and is registered to the PET dataset. An iterative reconstruction process is applied to the PET dataset using the MRI reconstructed image as guidance. The iterative reconstruction process includes one or more similarity coefficients and a spatially variant adaptive hyperparameter is calculated for each iteration of the iterative reconstruction process. A reconstructed image is output from the iterative reconstruction process.

11 Claims, 9 Drawing Sheets

(56) References Cited

OTHER PUBLICATIONS

Sudarshan, Viswanath P., et al. "Joint PET-MRI image reconstruction using a patch-based joint-dictionary prior." Medical image analysis 62 (2020): 101669. (Year: 2020).*

Yan, Jianhua, Jason Chu-Shern Lim, and David W. Townsend. "MRI-guided brain PET image filtering and partial volume correction." Physics in medicine & biology 60.3 (2015): 961. (Year: 2015).*

Defrise, M., Kinahan, P.E., Michel, C.J.: In: Bailey, D.L., Townsend, D.W., Valk, P.E., Maisey, M.N. (eds.) Image Reconstruction Algorithms in PET, pp. 63-91. Springer, London (2005).

Jinyi Qi, Leahy, R.M.: Resolution and noise properties of map reconstruction for fully 3-d pet. IEEE Transactions on Medical Imaging 19(5), 493-506 (2000). doi:10.1109/42.870259.

Nuyts, J., Beque, D., Dupont, P., Mortelmans, L.: A concave prior penalizing relative differences for maximum-a-posteriori reconstruction in emission tomography. IEEE Transactions on Nuclear Science 49(1), 56-60 (2002). doi:10.1109/TNS.2002.998681.

Tang, J., Rahmim, A.: Bayesian PET image reconstruction incorporating anato-functional joint entropy. Physics in Medicine and Biology 54(23), 7063-7075 (2009). doi:10.1088/0031-9155/54/23/002.

Bai, B., Li, Q., Leahy, R.M.: Magnetic resonance-guided positron emission tomography image reconstruction. Seminars in Nuclear Medicine 43(1), 30-44 (2013). doi:10.1053/j.semnuclmed.2012.08.006. PET/MRI.

Ehrhardt, M.J., Markiewicz, P., Liljeroth, M., Barnes, A., Kolehmainen, V., Duncan, J.S., Pizarro, L., Atkinson, D., Hutton, B.F., Ourselin, S., Thielemans, K., Arridge, S.R.: Pet reconstruction with an anatomical mri prior using parallel level sets. IEEE Transactions on Medical Imaging 35(9), 2189-2199 (2016). doi:10.1109/TMI.2016.2549601.

Mehranian, A., Belzunce, M.A., Niccolini, F., Politis, M., Prieto, C., Turkheimer, F., Hammers, A., Reader, A.J.: PET image reconstruction using multi-parametric anato-functional priors. Physics in Medicine & Biology 62(15), 5975-6007 (2017). doi:10.1088/1361-6560/aa7670.

Schramm, G., Holler, M., Rezaei, A., Vunckx, K., Knoll, F., Bredies, K., Boada, F., Nuyts, J.: Evaluation of parallel level sets and bowsher's method as segmentation-free anatomical priors for time-of-flight pet reconstruction. IEEE Transactions on Medical Imaging 37(2), 590-603 (2018). doi:10.1109/TMI.2017.2767940.

Tsai, Y.-J., Schramm, G., Ahn, S., Bousse, A., Arridge, S., Nuyts, J., Hutton, B.F., Stearns, C.W., Thielemans, K.: Benefits of using a spatially-variant penalty strength with anatomical priors in pet reconstruction. IEEE Transactions on Medical Imaging 39(1), 11-22 (2020). doi:10.1109/TMI.2019.2913889.

Kang, S.K., Lee, J.S.: Anatomy-guided PET reconstruction using l 1 bowsher prior. Physics in Medicine & Biology 66(9), 095010 (2021). doi:10.1088/1361-6560/abf2f7.

Meyer, H.S., Liesche-Starnecker, F., Mustafa, M., Yakushev, I., Wiestler, B., Meyer, B., Gempt, J.: [18f]fet pet uptake indicates high tumor and low necrosis content in brain metastasis. Cancers 13(2) (2021). doi:10.3390/cancers13020355.

Bowsher, J.E., Hong Yuan, Hedlund, L.W., Turkington, T.G., Akabani, G., Badea, A., Kurylo, W.C., Wheeler, C.T., Cofer, G.P., Dewhirst, M.W., Johnson, G.A.: Utilizing mri information to estimate f18-fdg distributions in rat flank tumors. In: IEEE Symposium Conference Record Nuclear Science 2004., vol. 4, pp. 2488-24924 (2004). doi:10.1109/NSSMIC.2004.1462760.

Salomon, A., Andreyev, A., Goedicke, A.: Information-adaptive denoising for iterative pet reconstruction. arXiv: Medical Physics (2019).

Reader, A.J., Ellis, S.: Bootstrap-optimised regularised image reconstruction for emission tomography. IEEE Transactions on Medical Imaging 39(6), 2163-2175 (2020). doi:10.1109/TMI.2019.2956878.

Vunckx, K., Atre, A., Baete, K., Reilhac, A., Deroose, C.M., Van Laere, K., Nuyts, J.: Evaluation of three mri-based anatomical priors for quantitative pet brain imaging. IEEE Transactions on Medical Imaging 31(3), 599-612 (2012). doi:10.1109/TMI.2011.2173766.

Kazantsev, D., Bousse, A., Pedemonte, S., Arridge, S.R., Hutton, B.F., Ourselin, S.: Edge preserving bowsher prior with nonlocal weighting for 3d spect reconstruction. In: 2011 IEEE International Symposium on Biomedical Imaging: From Nano to Macro, pp. 1158-1161 (2011). doi:10.1109/ISBI.2011.5872607.

Green, P.J.: On use of the em for penalized likelihood estimation. Journal of the Royal Statistical Society. Series B (Methodological) 52(3), 443-452 (1990).

Wang, G., Qi, J.: Penalized likelihood pet image reconstruction using patch-based edge-preserving regularization. IEEE Transactions on Medical Imaging 31(12), 2194-2204 (2012). doi:10.1109/TMI.2012.2211378.

De Pierro, A.R.: A modified expectation maximization algorithm for penalized likelihood estimation in emission tomography. IEEE Transactions on Medical Imaging 14(1), 132-137 (1995). doi:10.1109/42.370409.

Joshi, A.D., Pontecorvo, M.J., Lu, M., Skovronsky, D.M., Mintun, M.A., Devous, M.D.: A semiautomated method for quantification of f 18 florbetapir pet images. Journal of Nuclear Medicine 56(11), 1736-1741 (2015). doi: 10.2967/jnumed.114.153494. https://jnm.snmjournals.org/content/56/11/1736.full.pdf.

Poirier, Stefan E., et al., "An evaluation of the diagnostic equivalence of 18F-FDG-PET between hybrid PET/MRI and PET/CT in drug-resistant epilepsy: A pilot study", Epilepsy Research 172 (2021) 106583.

Poirier, Stefan E., et al., "18F-FDG PET-guided diffusion tractography reveals white matter abnormalities around the epileptic focus in medically refractory epilepsy: implications for epilepsy surgical evaluation", European Journal of Hybrid Imaging, (2020) 4:10, 19 pages, https://doi.org/10.1186/s41824-020-00079-7.

* cited by examiner

SYSTEMS AND METHODS OF GUIDED PET RECONSTRUCTION WITH ADAPTIVE PRIOR STRENGTH

BACKGROUND

The combination of magnetic resonance imaging (MRI)-anatomical information with positron emission tomography (PET) reconstruction has been shown to improve PET image quality in terms of spatial resolution and image noise. The combination of MRI image data, either acquired simultaneously or sequentially with PET image data, can potentially improve the spatial resolution and reduce image noise by guiding the PET image reconstruction.

The goal of combination PET and MRI reconstruction is to be generally segmentation-free, to avoid segmentation errors propagating into the PET image. Current MRI-guided PET reconstructions rely on an MRI sequence that is acquired during a PET/MRI scan. In some instances multiple sets of MRI images data can be used in a maximum a posteriori (MAP) reconstruction framework.

In current methods, a hyperparameter ($\beta$) is used to adjust for the influence of the anatomical information over measured information. The hyperparameter is selected prior to the reconstruction depending on the amount of measured data (e.g., net true counts) and to control the smoothness and image sharpness of the reconstructed image. Although some work has been done on optimizing the hyperparameter, current systems still require manual selection of a hyperparameter.

SUMMARY

In various embodiments, a system is disclosed. The system includes a positron emission tomography (PET) imaging modality configured to acquire a PET dataset, a magnetic resonance imaging (MRI) modality configured to acquire an MRI dataset, and a processor. An MRI reconstructed image is generated from the MRI dataset. The MRI reconstructed image is registered to the PET dataset. The processor is configured to receive the PET dataset and the MRI reconstructed image, apply an iterative reconstruction process to the PET dataset and the MRI dataset, calculate an adaptive hyperparameter for each iteration of the iterative reconstruction process, and output a reconstructed image from the iterative reconstruction process. The iterative reconstruction process includes one or more similarity coefficients.

In various embodiments, a method of generating a reconstructed clinical image is disclosed. The method includes the steps of obtaining a PET dataset, obtaining an MRI dataset, applying an iterative reconstruction process based on the PET dataset and the MRI dataset, calculating a spatially variant adaptive hyperparameter for each iteration of the iterative reconstruction process, and outputting a reconstructed image from the iterative reconstruction process. The MRI dataset is registered to the PET dataset and the iterative reconstruction process includes one or more similarity coefficients.

In various embodiments, a method of generating a reconstructed clinical image is disclosed. The method includes the steps of obtaining a PET dataset, obtaining an MRI dataset, applying an iterative reconstruction process based on the PET dataset and the MRI dataset, calculating an adaptive hyperparameter for each iteration of the iterative reconstruction process, and outputting a reconstructed image from the iterative reconstruction process. The MRI dataset is registered to the PET dataset and the iterative reconstruction process comprises an optimization algorithm and a potential function.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

This description of the exemplary embodiments is intended to be read in connection with the accompanying drawings, which are to be considered part of the entire written description.

In the following, various embodiments are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the systems.

Furthermore, in the following, various embodiments are described with respect to methods and systems for reconstructing clinical images from PET and MRI scan data using an adaptive hyperparameter. In some embodiments, the adaptive hyperparameter is based on image noise determined at each iteration for every voxel in the PET scan data. The adaptive hyperparameter is configured to control the influence of the MRI scan data on the PET scan data during reconstruction. The adaptive hyperparameter can be implemented in conjunction with information-theory-based similarity coefficients. The disclosed embodiments improve image quality, such as resolution and noise, across different levels of statistics within the PET and MRI scan data while retaining unique features of PET-based reconstructions.

Figure 1:
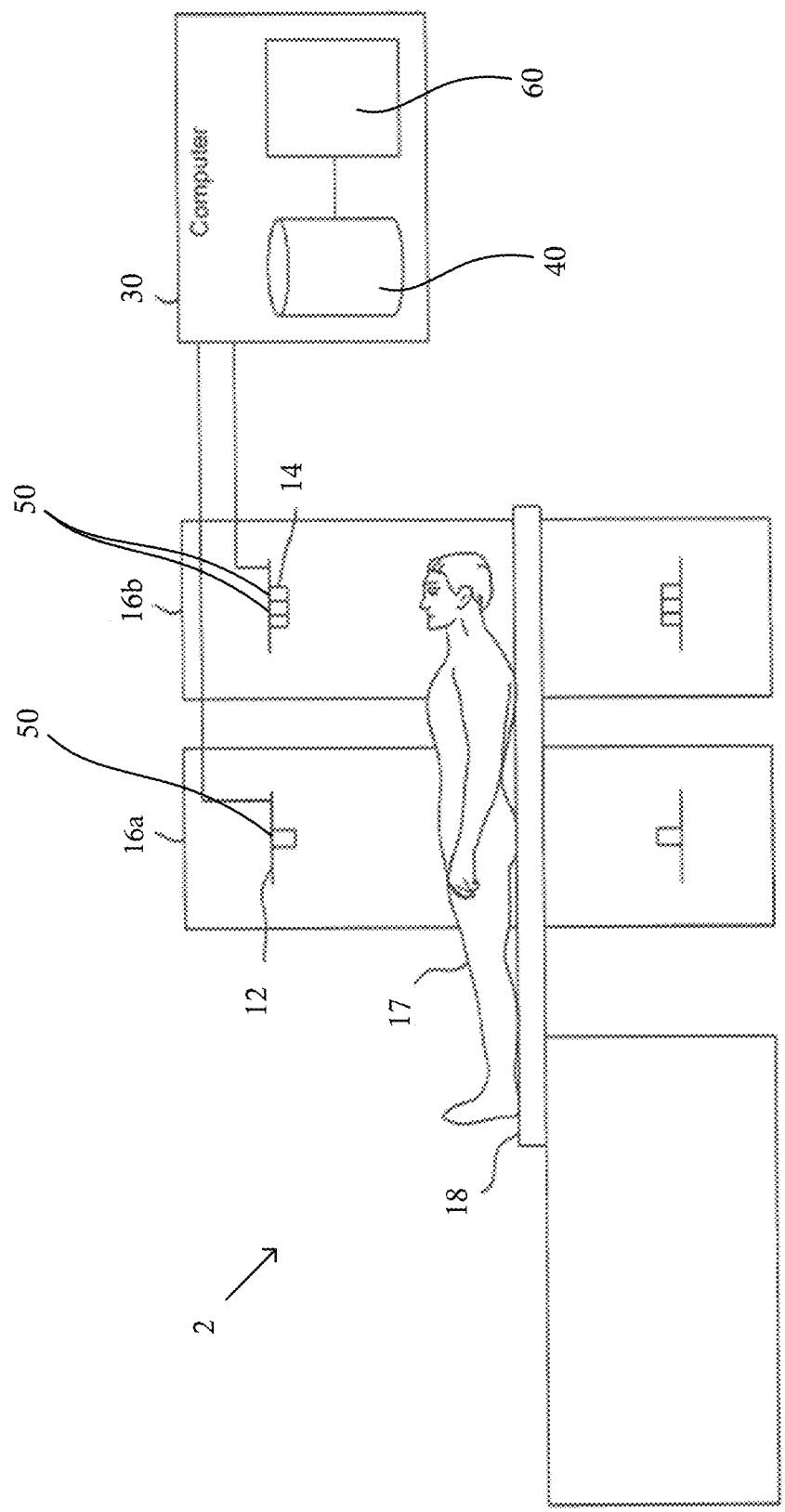
FIG. 1 illustrates a nuclear imaging system, in accordance with some embodiments.

FIG. 1 illustrates one embodiment of a nuclear imaging system 2, in accordance with some embodiments. The nuclear imaging system 2 includes a scanner for at least a first modality 12 provided in a first gantry 16a. The first modality 12 can include any suitable imaging modality, such as a positron emission tomography (PET) modality. A patient 17 lies on a movable patient bed 18 that can be movable within a gantry 19. In some embodiments, the nuclear imaging system 2 includes a scanner for a second imaging modality 14 provided in a second gantry 16b. The second imaging modality 14 can be any suitable imaging modality, such as, for example, a magnetic resonance imaging (MRI) modality. Although embodiments are discussed herein including an MRI modality, it will be appreciated that any suitable modality configured to provide sufficient soft tissue contrast and spatial resolution can be used. Each of the first modality 12 and/or the second modality 14 can include one or more detectors 50 configured to detect an annihilation photon, gamma ray, and/or other nuclear imaging event.

Scan data from the first modality 12 and/or the second modality 14 is stored at one or more computer databases 40 and processed by one or more computer processors 60 of a computer system 30. The graphical depiction of computer system 30 in FIG. 1 is provided by way of illustration only, and computer system 30 can include one or more separate computing devices. The nuclear imaging data sets can be provided by the first modality 12, the second modality 14, and/or can be provided as a separate data set (e.g., reconstructed image(s), list mode data set(s), raw data, etc.), such as, for example, from a memory coupled to the computer system 30. The computer system 30 can include one or more processing electronics for processing a signal received from one of the plurality of detectors 50.

In some embodiments, the computer system 30 is configured to generate reconstructed images based on image data from the first modality 12 and image data from the second modality 14. For example, in some embodiments, the computer 30 is configured to generate reconstructed images based on PET imaging data and MRI imaging data. The obtained image data can be acquired sequentially and/or at least partially simultaneously. The reconstructed images can be generated using an iterative reconstruction process including an adaptive hyperparameter (i.e., an adaptive prior strength parameter).

Figure 2:
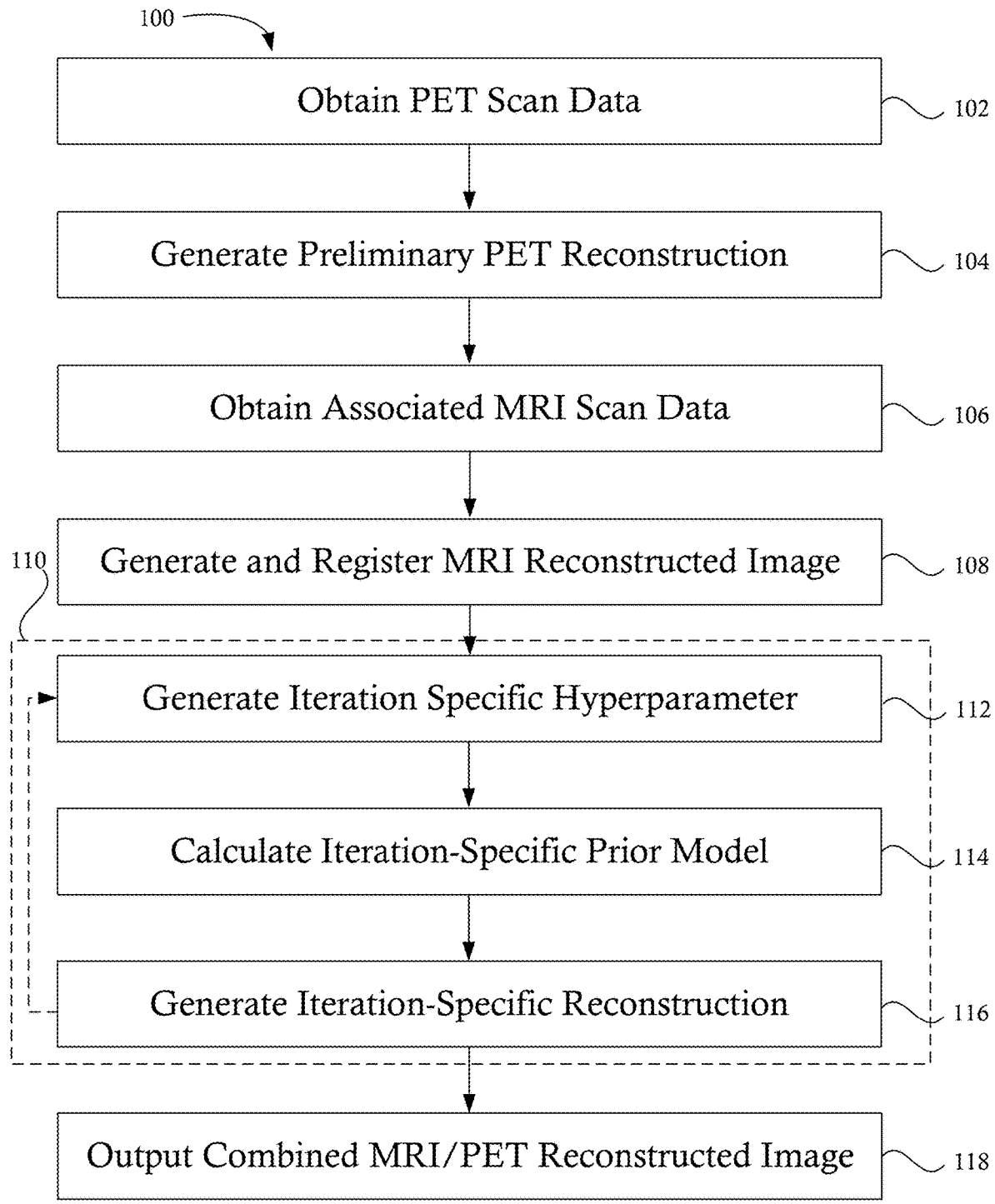
FIG. 2 is a flowchart illustrating a method of generating an image reconstruction using an adaptive hyperparameter, in accordance with some embodiments.

FIG. 2 is a flowchart 100 illustrating a method of reconstructing a clinical image from PET and MRI scan data using an adaptive hyperparameter, in accordance with some embodiments. At step 102, PET scan data is obtained and, at step 104, a preliminary PET image reconstruction is generated. The preliminary PET image reconstruction can be generated using any suitable reconstruction process. In some embodiments, step 104 is omitted and the iterative process discussed below is applied directly to the PET image data. Similarly, at step 106, MRI scan data associated with the PET scan data is obtained and, at step 108, an MRI reconstruction is generated and registered to the preliminary PET image. The PET scan data and/or the MRI scan data can be obtained using any suitable mechanism, such as, for example, the nuclear imaging system 2 illustrated in FIG. 1. Although steps 102-108 are illustrated sequentially, it will be understood that the PET scan data and the MRI scan data can be obtained in any suitable manner, for example, being obtained partially and/or substantially simultaneously, sequentially (e.g., the MRI scan data being obtained during the same imaging sessions and within a predetermined time period before or after the PET scan data), and/or according to any other suitable acquisition protocol. Similarly, it will be appreciated that generation of the preliminary PET reconstruction and the MRI reconstruction can occur sequentially, simultaneously, or at different times.

At step 110, an iterative reconstruction process is implemented. Where a set of scan data includes a set of measurements (y), and a measured activity distribution (u), a Bayesian maximum a posteriori (MAP) reconstruction attempts to maximize the logarithm posterior probability of u:

$$\hat{u} = \mathrm{argmax}\{\log p(y,u) + \log p(u)\}$$

where p(u) can be modeled as a Gibbs distribution $\exp^{-\beta R(u)}$, where $\beta$ is a hyperparameter controlling the strength of the additional information over the acquired data and $R(u)$ is the prior model in an iterative process. $R(u)$ can be expressed in a general form as:

$$R(u) = \sum_{j}^{N} \phi\left(\sum_{b \in N_j} \xi_{jb} \omega_{jb} \psi(u_j - u_b)\right)$$

where j is a voxel index, b is an index for the voxels in a neighborhood $N_j$, N is a number of voxels, $\phi$ is a function operating in $N_j$, $\xi$ is a proximity coefficient, $\omega$ is a similarity coefficient, and $\psi$ is a function that defines a relation between each voxel and its neighbors. Various potential functions, weights for a specific potential function (similarity coefficients), and/or different optimization algorithms can be applied based on the foregoing equation. In some embodiments, the p(u) term can be dropped from the logarithm posterior probability equation, which reduces the equation to a maximum-likelihood expectation-maximization (MLEM) equation or an ordered-subsets expectation-maximization (OSEM).

$\psi(u)$ can include any suitable function. For example, in various embodiments, $\psi(u)$ can include a quadratic difference (PFQ) function, a relative difference (RD) function, and/or any other suitable function. The PFQ function can be defined by the equation:

$$\psi(u_j - u_b) = (u_j - u_b)^2$$

and the RD equation can be defined as:

$$\psi(u_j - u_b) = \frac{(u_j - u_b)^2}{u_j + u_b}$$

In some embodiments, the RD and/or PFQ functions can be used in conjunction with a Bowsher similarity coefficient (Bw). Although various embodiments are discussed herein, it will be appreciated that any suitable function $\psi(u)$ can be used to define the relation between each voxel and its neighbors.

In some embodiments, the similarity coefficient $\omega$ is configured to weigh a potential between two voxels based on their intensity similarities. For example, in some embodiments, $\omega$ can be based on MRI scan data, with $\omega=1$ where the voxels are considered similar and $\omega=0$ otherwise. Whether two voxels are similar can be determined based on a fixed number of voxel-pairs, where the voxel-pair(s) having the lowest intensity difference in the scan data are considered similar. In some embodiments, a predetermined intensity difference threshold can be used to determine similarity. In other embodiments, the intensity difference threshold can be determined based on a mean, max, average, or other statistical value of the voxel-pairs in the MRI image. In some embodiments, a predetermined region of interest (ROI) size and/or a fixed number of voxel pairs in the comparison can be predetermined.

In some embodiments, the similarity coefficient $\omega$ is determined based on an intensity difference histogram of $u_j$ and each voxel in $N_j$. Voxels $u_b$ that correspond to the first bin of the calculated histogram can be considered in the calculation of the prior (e.g., the a priori calculation). Use of an intensity difference histogram prevents the use of a fixed number of voxels in $N_j$ and allows for adaptation to edges and uniform regions within the scan data. In some embodiments, the initial size of the ROI for generating the intensity difference histogram can be a fixed size, such as, for example, a 7×7×7 voxel region, although it will be appreciated that any suitable region size can be used. In some embodiments, a similarity coefficient is independently calculated for each voxel at each iteration.

In some embodiments, the similarity coefficient $\omega$ can be based on a Bowsher weight (Bw) and/or a Burg joint entropy weight (JEw). In such embodiments, the similarity coefficient can be defined as:

$$\omega_{jb} = \frac{1}{p(u_j, v_j)} \exp\left(-\frac{(u_j - u_b)^2}{2\sigma_u^2}\right) \prod_k \exp\left(-\frac{(v_j^{(k)} - v_b^{(k)})^2}{2\sigma_{v(k)}^2}\right)$$

where v is MRI scan data, k is the index of the MRI sequence from the multi-parametric approach, $\sigma$ is the standard deviation in $N_j$ in u and v, and $p(u_j, v_j)$ is defined as a non-parametric Parzen window using Gaussian kernels. In some embodiments, $p(u_j, v_j)$ can be defined as:

$$p(u_j, v_j) = \sum_{b \in N_j} \frac{1}{\sigma_u \sqrt{2\pi}} \left(-\frac{(u_j - u_b)^2}{2\sigma_u^2}\right) \left|\sum_k \frac{1}{\sigma_v^{(k)} \sqrt{2\pi}} \exp\left(\frac{(v_j^{(k)} - v_b^{(k)})^2}{2\sigma_{v(k)}^2}\right)\right.$$

In some embodiments, an optimization algorithm can be selected to maximize a cost function. For example, in some embodiments, a one-step-late (OSL) algorithm, a modified gradient ascent method (PGA), a MLEM algorithm, and/or a penalized likelihood based on a separable surrogate (PLSS) algorithm. Although specific embodiments are discussed herein, it will be appreciated that any suitable optimization algorithm can be used.

In some embodiments, an OSL optimization algorithm can be defined as:

$$u_j^{n+1} = \frac{u_j^n}{\sum_{i=1}^M g_{ij} n_i a_i - \beta \frac{\partial R(u^n)}{\partial u_j}} \sum_{i=1}^M g_{ij} n_i a_i \frac{y_i}{n_i a_i \sum_b g_{ib} u_b^n + r_i}$$

where i is a line-of-response (LOR) index, M is a number of LORs, $r_i$ is scatter and random coincidences, $n_i$ is a normalization, $a_i$ is attenuation factors, and $g_{ij}$ is a system matrix. In some embodiments, a preconditioned gradient ascent (PGA) MLEM algorithm can be defined as:

$$u_j^{n+1} = \frac{u_j^n}{\sum_{i=1}^M g_{ij} n_i a_i} \sum_{i=1}^M g_{ij} n_i a_i \frac{y_i}{n_i a_i \sum_b g_{ib} u_b^n + r_i} + \beta \frac{\partial R(u^n)}{\partial u_j}$$

As another example, in some embodiments, a PLSS algorithm can be defined as:

$$u_j^{n+1} = \frac{2 u_{j,EM}^{n+1}}{(1 - \beta u_{j,reg}^{n+1}) + \sqrt{(1 - \beta u_{j,reg}^{n+1})^2 + 4\beta u_{j,reg}^{n+1}}}$$

where $u_{j,EM}^{n+1}$ is the expectation-maximization estimate of $u_j^n$ smoothed according to the equation:

$$u_{j,reg}^{n+1} = \frac{1}{2 \sum_{b \in N_j} \omega_{jb}} \sum_{b \in N_j} \omega_{jb} (u_{j,EM}^n + u_{b,EM}^n)$$

At sub-step 112, an iteration-specific hyperparameter $\beta$ (e.g., an adaptive hyperparameter) is calculated based on the noise in each image voxel for the current iteration. For example, during the initial iteration of step 104, the noise in each image voxel will be the noise in the raw scan data. During subsequent iterations (as discussed below) the noise in each image voxel may be different due to the noise amplification and propagation during the reconstruction process, resulting in high frequency noise in the image at each subsequent iteration. An adaptive hyperparameter can be calculated using any suitable algorithm and/or method for determining a hyperparameter applied to the current iteration and/or one or more features of the current iteration. In some embodiments, the adaptive hyperparameter includes a spatially variant adaptive hyperparameter.

In some embodiments, a hyperparameter $\beta_j$ is calculated as:

$$\beta_j = \alpha \sqrt{u_j \sum_{i=1}^{M} y_{ij} n_i a_i}$$

where $\alpha$ is a constant, u is a measured activity distribution, j is a voxel index, i is a line-of-response (LOR) index, M is the number of LORs, $n_i$ is a normalization, and $a_i$ are attenuation factors. At each iteration, one or more factors in the above equation vary based on the prior iteration and an adapted, iteration-specific value is calculated for each reconstruction iteration. In some embodiments including a OSL algorithm, an iteration-specific hyperparameter can be set to zero when a prior dominates over a sensitivity in a per-voxel basis, effectively converting the OSL reconstruction to an OSEM reconstruction.

At sub-step 114, a calculation is performed using an iterative-specific version of the selected prior model that incorporates the iterative-specific adaptive hyperparameter $\beta$. The iterative-specific prior model at sub-step 114 generates an iteration specific reconstruction (e.g., updated PET and/or MRI scan data), which is output at sub-step 116 for use in subsequent iterations of the iterative reconstruction process 110 and/or for generation of a reconstructed image. The iterative reconstruction process 110 can iterate a predetermined number of times. The predetermined number of iterations can be set based on, for example, the prior model selected, the scan time for the PET scan data and/or the corresponding MRI scan data, the clinical purpose of the reconstruction, and/or any other suitable parameters. Although sub-steps 112-116 are illustrated sequentially, it will be understood that the sub-steps can be performed in any order and/or can be integrated into a single step. For example, in some embodiments, generation of an iteration-specific hyperparameter can be performed as part of an iterative-specific prior model.

At step 118, one or more reconstructed images are generated and output based on the output data generated by the iterative reconstruction process. In some embodiments, the generated reconstruction images are the final iteration-specific reconstructions generated by the iterative reconstruction process 110. The reconstructed images can be generated using any suitable process for converting the iteratively-processed scan data to a visual image, as is known in the art. The one or more reconstructed images include clinical images suitable for one or more clinical applications. For example, in some embodiments, the reconstructed images can be configured for diagnostic review, planning, and/or any other clinical purpose. As discussed further below, the use of an adaptive hyperparameter allows integration between PET and MRI scan data to provide a higher resolution and higher accuracy reconstructed image.

Figure 3C:
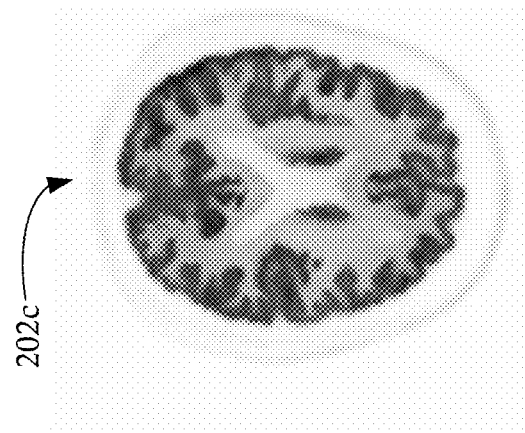
FIG. 3C illustrates an image reconstruction generated according to an adaptive hyperparameter process from simulated five-minute scan data, in accordance with some embodiments.
Figure 3B:
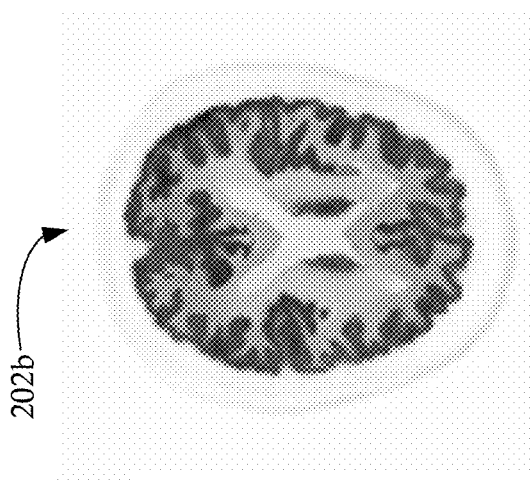
FIG. 3B illustrates an image reconstruction generated according to a fixed hyperparameter process from simulated five-minute scan data.
Figure 3A:
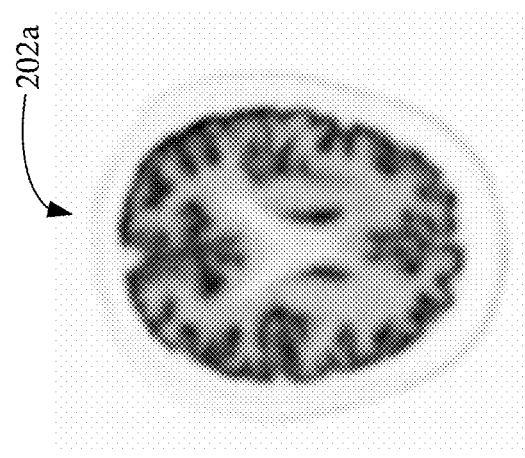
FIG. 3A illustrates an image reconstruction generated according to an ordered-subsets expectation-maximization process from simulated five-minute scan data.
Figure 4C:
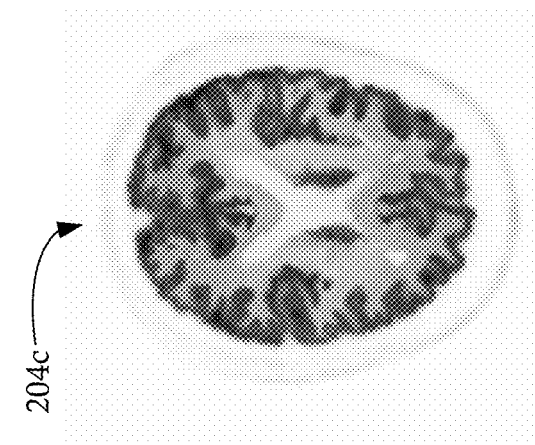
FIG. 4C illustrates an image reconstruction generated according to an adaptive hyperparameter process from simulated one-minute scan data, in accordance with some embodiments.
Figure 4B:
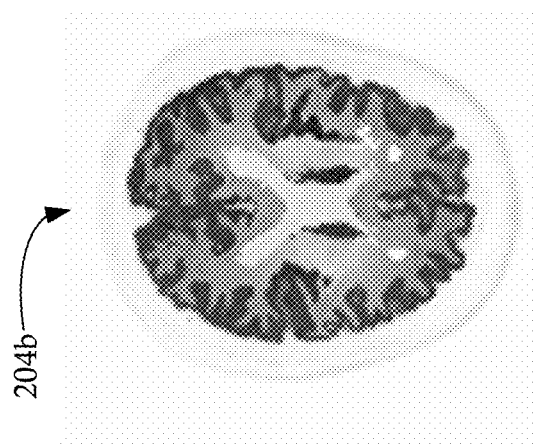
FIG. 4B illustrates an image reconstruction generated according to a fixed hyperparameter process from simulated one-minute scan data.
Figure 4A:
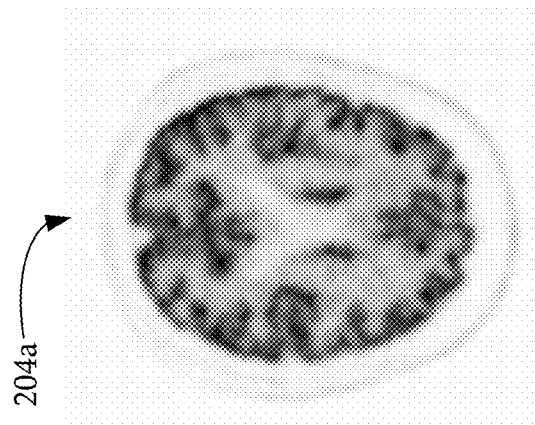
FIG. 4A illustrates an image reconstruction generated according to an ordered-subsets expectation-maximization process from simulated one-minute scan data.

FIGS. 3A-3C illustrate a comparison of image reconstructions 202a, 202b, 202c generated for according to three different processes, a reconstruction 202a according to a traditional OSEM process, a reconstruction 202b using information-theory-based similarity coefficients with a fixed hyperparameter, and a reconstruction 202c using information-theory-based similarity coefficients with an adaptive hyperparameter. The PET and MRI scan data used for the image reconstructions 202a-202c included simulated scan data for a central axial slice over a five minute scan period. Similarly, FIGS. 4A-4C illustrate a comparison of image reconstructions 204a, 204b, 204c generated for according to three different processes, a reconstruction 204a according to a traditional OSEM process, a reconstruction 204b using information-theory-based similarity coefficients with a fixed hyperparameter, and a reconstruction 204c using information-theory-based similarity coefficients with an adaptive hyperparameter. The PET and MRI scan data used for the image reconstructions 204a-204c included simulated scan data for a central axial slice over a one minute scan period.

As shown in FIGS. 3A-4C, the reconstructions 202c, 204c generated using a reconstruction process including an adaptive hyperparameter, as described above with respect to FIG. 2, includes a higher image quality as compared to the other reconstructions 202a-202b, 204a-204b using similar scan data. In some embodiments, the difference between the reconstructions 202a-204c can be evaluated for different cortical and sub-cortical regions based on a Hammer atlas. As shown, the adaptive hyperparameter reconstructions 202c, 204c have improved lesion detection/illustration due to the incorporation of MRI sequence data containing lesion data. The spatial resolution of the adaptive hyperparameter reconstructions 202c, 204c is higher and the noise present in the adaptive hyperparameter reconstructions 202c, 204c is lower as compared to the other reconstructions 202a-202b, 204a-204b. The mean intensity measured in analyzed regions of the adaptive hyperparameter reconstructions 202c, 204c, for the five minute scan period is similar to that obtained by a 20 minute scan using traditional techniques, demonstrating the improved image quality provided by the adaptive hyperparameter reconstruction. In addition, the adaptive hyperparameter reconstructions 202c, 204c generated using scan data obtained over shorter periods (e.g., the five minute scan period) provide similar noise profiles as compared to non-adaptive reconstructions generated using scan data obtained over longer scan (e.g., the twenty minute scan period). Thus, the use of an adaptive hyperparameter reconstruction allows faster scans and/or lower doses of tracers as compared to non-adaptive reconstruction techniques.

The disclosed adaptive hyperparameter systems can be used to increase resolution over shorter scan periods, improve resolution of scans including both MRI and PET data, allow for reduced doses of tracer materials due to shorter scan times or higher resolution imaging, disease progression tracking over multiple scans, extraction of image-driven input functions for dynamic analysis of radiotracers, and/or other clinical applications. In some embodiments, two or more MRI sequences can be used in a reconstruction.

Figure 5B:
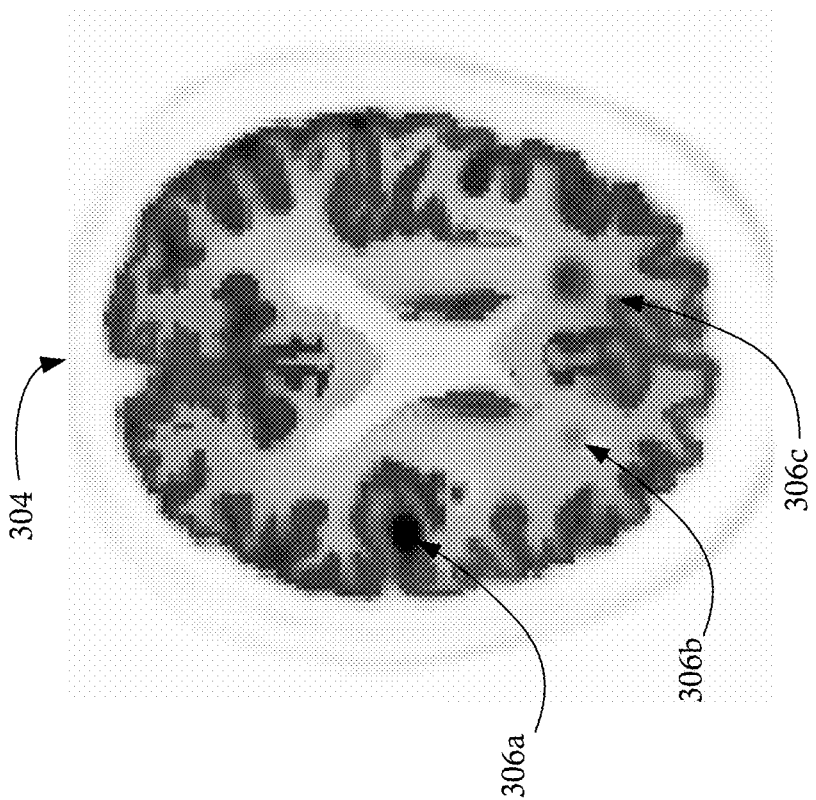
FIG. 5B illustrates a reconstruction according to an adaptive hyperparameter process from simulated scan data over a five minute period having lesion data only in simulated PET scan data, as disclosed herein.
Figure 5A:
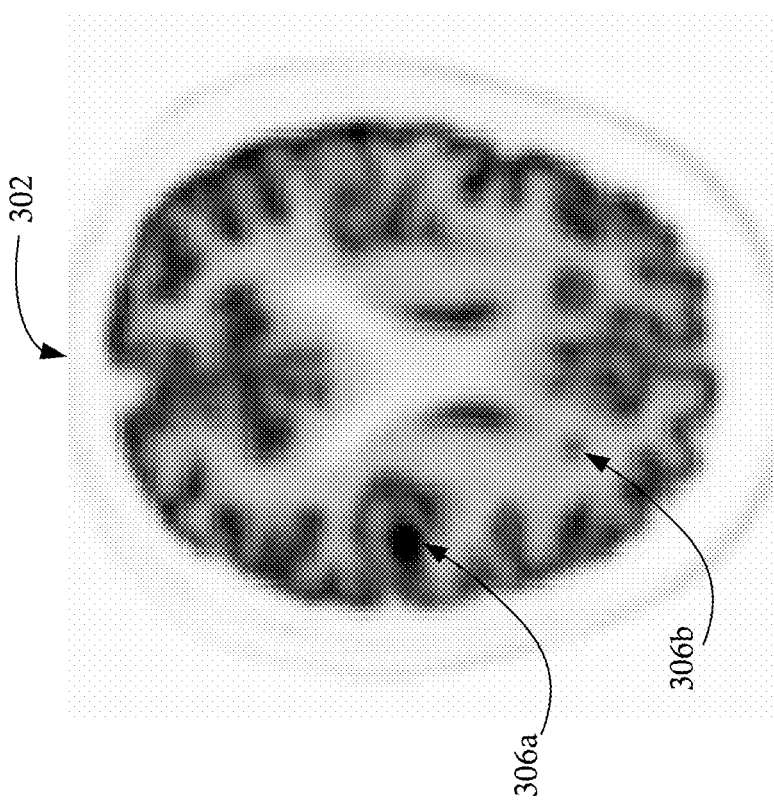
FIG. 5A illustrates a reconstruction according to an ordered-subsets expectation-maximization process from simulated scan data over a five minute period having lesion data only in simulated PET scan data.

FIGS. 5A and 5B illustrate reconstructions of simulated scan data over a five minute period in which 3 lesions present only in the PET scan data. FIG. 5A illustrates a reconstruction 302 according to an OSEM process and FIG. 5B illustrates a reconstruction 304 according to an adaptive hyperparameter process, as disclosed herein. As illustrated in FIG. 5A, two lesions 306a-306b are somewhat visible based on the OSEM reconstruction 302. The adaptive hyperparameter reconstruction 304 of FIG. 5B includes the two lesions 306a-306b visible in the OSEM reconstruction 302 of FIG. 5A, but the lesions 306a-306b are clearer and more easily identified in the adaptive hyperparameter reconstruction 304. In addition, the adaptive hyperparameter reconstruction 304 includes a lesion 306c that is absent (or so obscured by noise so as to be indiscernible) in FIG. 5A. The adaptive hyperparameter reconstruction 304 provides an improvement in image quality allowing identification and diagnosis of clinically important information beyond that provided by the OSEM reconstruction 302. FIG. 5B also illustrates a generally higher spatial resolution of the adaptive hyperparameter reconstruction 304, having a clearer image in general as compared to the OSEM reconstruction 302.

Figure 7A:
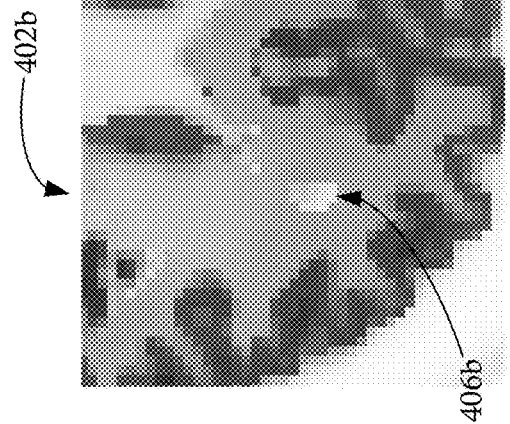
FIG. 7A illustrates a reconstruction according to fixed hyperparameter process from simulated scan data over a one minute period having lesion data only in simulated PET scan data.
Figure 7B:
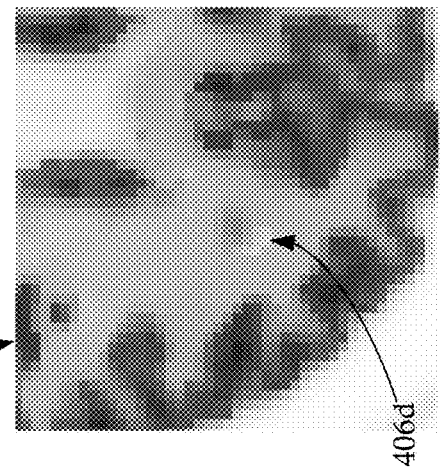
FIG. 7B illustrates a reconstruction according to an adaptive hyperparameter process from simulated scan data over a one minute period having lesion data only in simulated PET scan data, as disclosed herein.
Figure 6A:
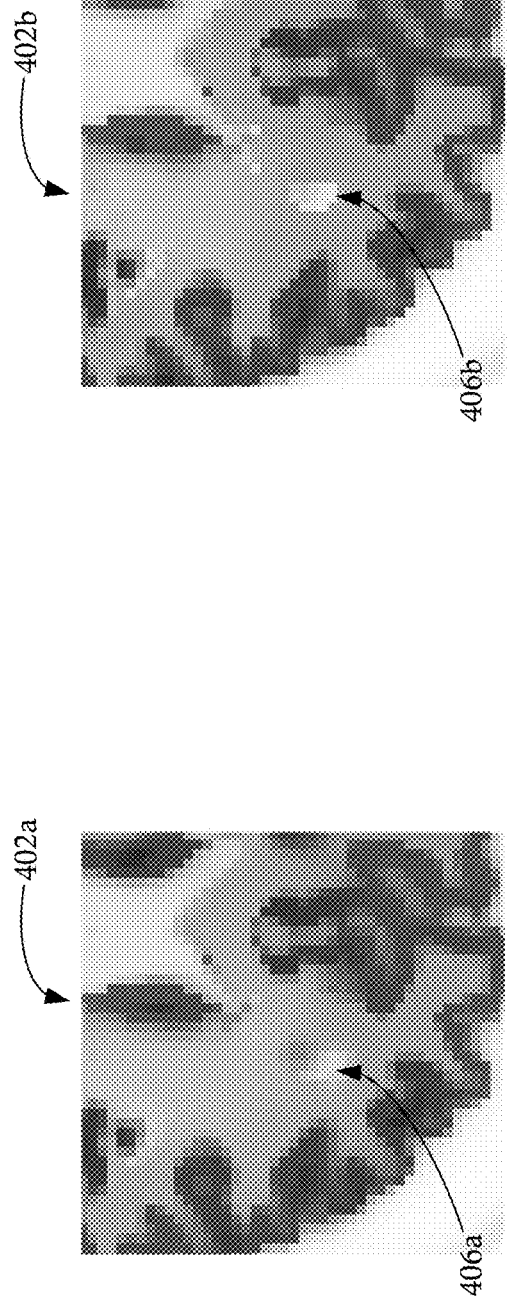
FIG. 6A illustrates a reconstruction according to fixed hyperparameter process from simulated scan data over a five minute period having lesion data only in simulated PET scan data.
Figure 6B:
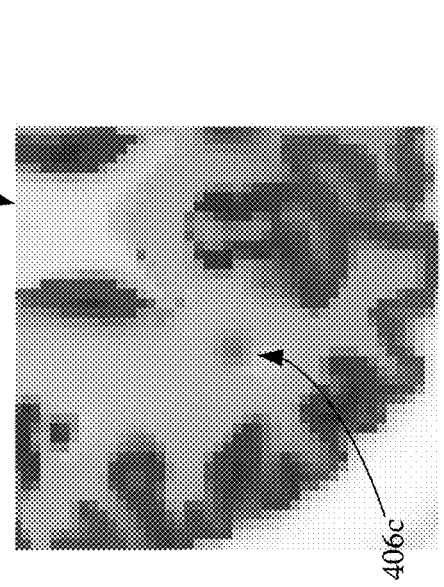
FIG. 6B illustrates a reconstruction according to an adaptive hyperparameter process from simulated scan data over a five minute period having lesion data only in simulated PET scan data, as disclosed herein.

FIGS. 6A and 6B illustrate reconstructions of simulated scan data over a five minute period in which a lesion is present only in the PET scan data. FIG. 6A illustrates a reconstruction 402a according to fixed hyperparameter process and FIG. 6B illustrates a reconstruction 404a according to an adaptive hyperparameter process, as disclosed herein. Similarly, FIGS. 7A and 7B illustrate reconstructions of simulated scan data over a one minute period in which a lesion is present only in the PET scan data. FIG. 7A illustrates a reconstruction 402b according to fixed hyperparameter process and FIG. 7B illustrates a reconstruction 404b according to an adaptive hyperparameter process, as disclosed herein. As can be seen in FIGS. 6A and 7A, the five-minute fixed hyperparameter reconstruction 402a and the five-minute adaptive hyperparameter reconstruction 404a both illustrate a lesion 406 with the adaptive hyperparameter reconstruction 404a having a slightly higher spatial resolution. As shown in FIG. 7B, the lesion 406 can also clearly be seen in the one-minute adaptive hyperparameter reconstruction 404b, but is absent or obscured in the one-minute fixed hyperparameter reconstruction 402b of FIG. 6B.

Figure 8B:
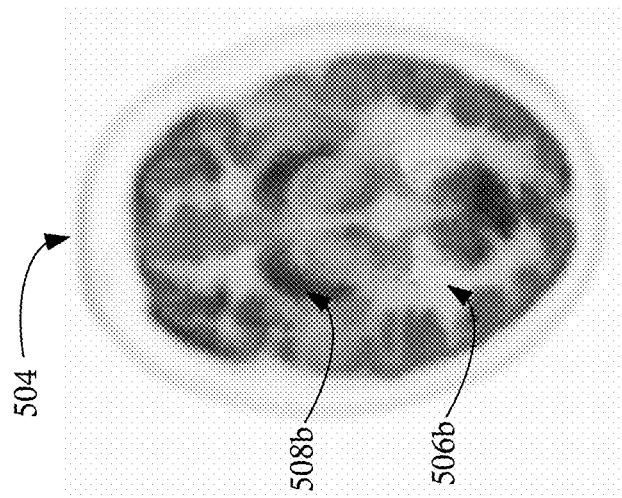
FIG. 8B illustrates a reconstruction according to an adaptive hyperparameter process from PET scan data obtained over a thirty minute scan period and MRI scan data registered to the PET scan data, in accordance with some embodiments.
Figure 8A:
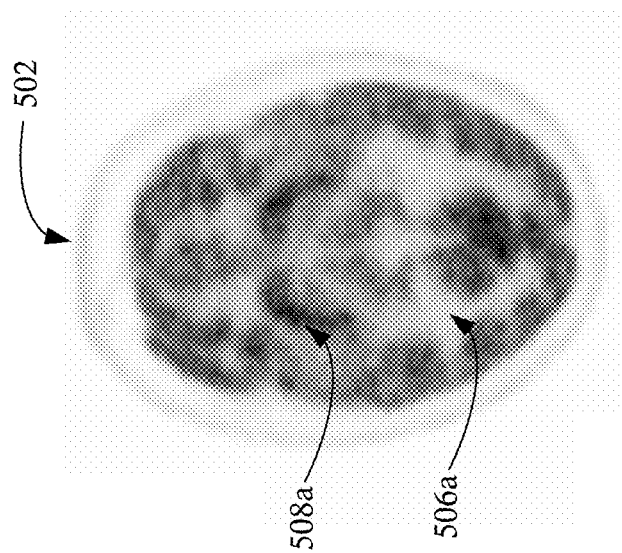
FIG. 8A illustrates a reconstruction according to an ordered-subsets expectation-maximization process from PET scan data obtained over a thirty minute scan period and MRI scan data registered to the PET scan data.

FIGS. 8A and 8B illustrate reconstructions for a combined PET/MRI scan performed on a patient with epilepsy. The PET scan data was obtained using a fluorodeoxyglucose-based PET scan and MRI scan data was registered to the PET scan data. The PET scan data was obtained over a thirty-minute interval and included some movement of the patient during the scan. FIG. 8A illustrates a reconstruction 502 according to an OSEM process and FIG. 8B illustrates a reconstruction 504 according to an adaptive hyperparameter process, in accordance with some embodiments. As shown in FIGS. 8A and 8B, the adaptive hyperparameter reconstruction 504 has a higher spatial resolution resulting in a clearer image in areas 506b, 508b as compared to the same regions 506a, 508a in the OSEM reconstruction 502.

Figure 9A:
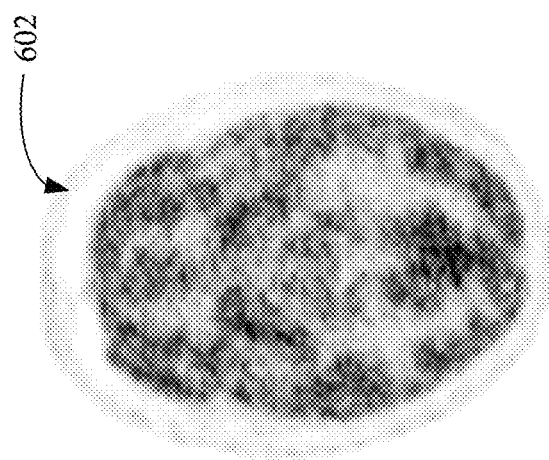
FIG. 9A illustrates a reconstruction according to an ordered-subsets expectation-maximization process from PET scan data for a five-minute period and MRI scan data registered to the PET scan data.
Figure 9C:
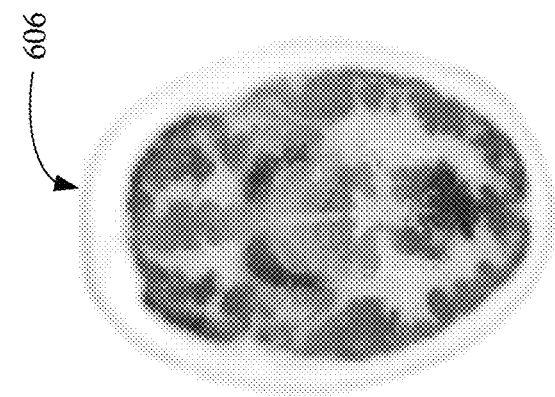
FIG. 9C illustrates a reconstruction according to an adaptive hyperparameter process from PET scan data for a five-minute period and MRI scan data registered to the PET scan data, in accordance with some embodiments.
Figure 9B:
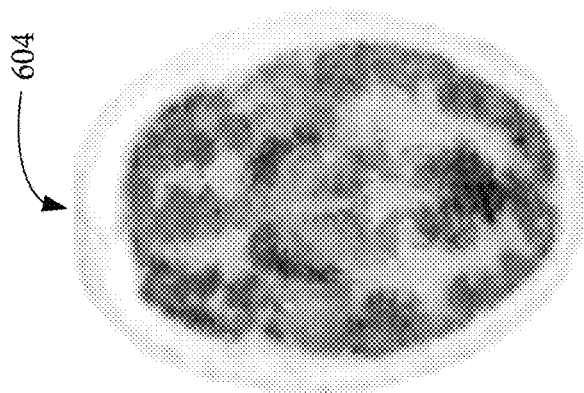
FIG. 9B illustrates a reconstruction according to an adaptive hyperparameter process from PET scan data for a five-minute period and MRI scan data without registration to the PET scan data, in accordance with some embodiments.

FIGS. 9A-9C illustrate reconstructions for a five-minute portion of the scan data of the patient with epilepsy previously discussed with respect to FIGS. 8A-8B. FIG. 9A illustrates a reconstruction 602 according to an OSEM process, FIG. 9B illustrates a reconstruction 604 using an adaptive hyperparameter without alignment of the PET and MRI (resulting in degradation due to patient motion), and FIG. 9C illustrates a reconstruction 606 according to an adaptive hyperparameter with PET/MRI registration. Similar to the thirty minute reconstructions shown in FIGS. 8A and 8B, the adaptive hyperparameter reconstructions 604, 606 of FIGS. 9B and 9C have higher spatial resolution resulting in clearer images as compared to the OSEM reconstruction 602 in FIG. 9A. FIG. 9C has lower noise and better definition as compared to FIG. 9B, illustrating an improvement in image quality due to PET and MRI registration. FIG. 9C provides much lower noise and higher spatial resolution as compared to FIG. 9A. In the illustrated embodiments, FIG. 9A does not have enough image quality to be used clinically, whereas FIG. 9C has sufficient image quality to be used clinically. FIG. 9C shows no degradation as compared to FIG. 8B, which is a reconstruction from scan data acquired over a thirty minute period. Thus, the adaptive hyperparameter process disclosed herein provides for reduced scan time without affecting image quality required clinically for appropriate diagnosis.

Figure 10:
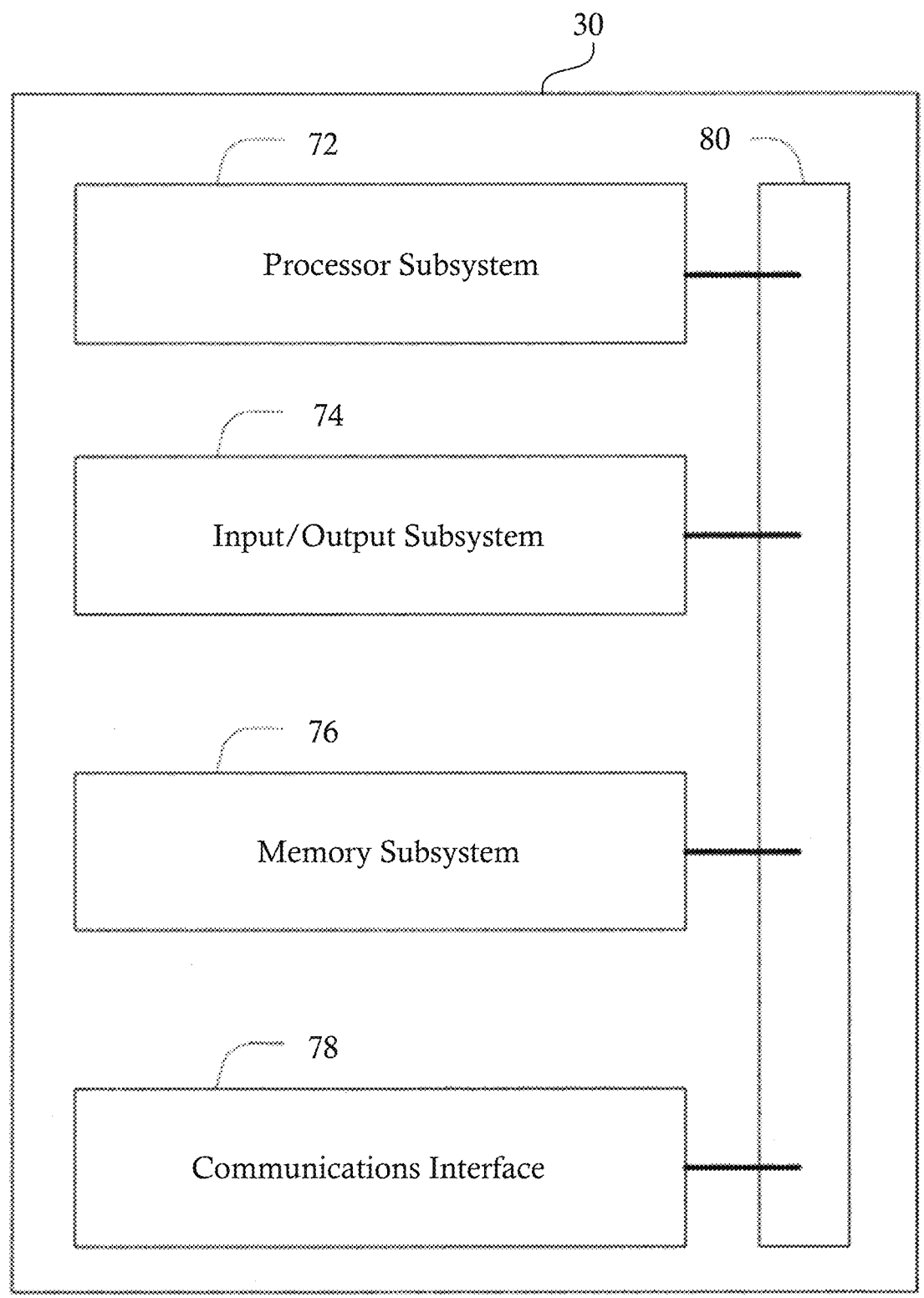
FIG. 10 illustrates a computer system configured to implement one or more processes, in accordance with some embodiments.

FIG. 10 illustrates a computer system 30 configured to implement one or more processes, in accordance with some embodiments. The system 30 is a representative device and can include a processor subsystem 72, an input/output subsystem 74, a memory subsystem 76, a communications interface 78, and a system bus 80. In some embodiments, one or more than one of the system 30 components can be combined or omitted such as, for example, not including an input/output subsystem 74. In some embodiments, the system 30 can comprise other components not shown in FIG. 10. For example, the system 30 can also include, for example, a power subsystem. In other embodiments, the system 30 can include several instances of a component shown in FIG. 10. For example, the system 30 can include multiple memory subsystems 76. For the sake of conciseness and clarity, and not limitation, one of each component is shown in FIG. 10.

The processor subsystem 72 can include any processing circuitry operative to control the operations and performance of the system 30. In various aspects, the processor subsystem 72 can be implemented as a general purpose processor, a chip multiprocessor (CMP), a dedicated processor, an embedded processor, a digital signal processor (DSP), a network processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor subsystem 72 also can be implemented by a controller, a microcontroller, an application specific integrated circuit (ASIC), a field programmable gate array (FPGA), a programmable logic device (PLD), and so forth.

In various aspects, the processor subsystem 72 can be arranged to run an operating system (OS) and various applications. Examples of an OS comprise, for example, operating systems generally known under the trade name of Apple OS, Microsoft Windows OS, Android OS, Linux OS, and any other proprietary or open source OS. Examples of applications comprise, for example, network applications, local applications, data input/output applications, user interaction applications, etc.

In some embodiments, the system 30 can include a system bus 80 that couples various system components including the processing subsystem 72, the input/output subsystem 74, and the memory subsystem 76. The system bus 80 can be any of several types of bus structure(s) including a memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect Card International Association Bus (PCM-CIA), Small Computers Interface (SCSI) or other proprietary bus, or any custom bus suitable for computing device applications.

In some embodiments, the input/output subsystem 74 can include any suitable mechanism or component to enable a user to provide input to system 30 and the system 30 to provide output to the user. For example, the input/output subsystem 74 can include any suitable input mechanism, including but not limited to, a button, keypad, keyboard, click wheel, touch screen, motion sensor, microphone, camera, etc.

In some embodiments, the input/output subsystem 74 can include a visual peripheral output device for providing a display visible to the user. For example, the visual peripheral output device can include a screen such as, for example, a Liquid Crystal Display (LCD) screen. As another example, the visual peripheral output device can include a movable display or projecting system for providing a display of content on a surface remote from the system 30. In some embodiments, the visual peripheral output device can include a coder/decoder, also known as Codecs, to convert digital media data into analog signals. For example, the visual peripheral output device can include video Codecs, audio Codecs, or any other suitable type of Codec.

The visual peripheral output device can include display drivers, circuitry for driving display drivers, or both. The visual peripheral output device can be operative to display content under the direction of the processor subsystem 72. For example, the visual peripheral output device can be able to play media playback information, application screens for application implemented on the system 30, information regarding ongoing communications operations, information regarding incoming communications requests, or device operation screens, to name only a few.

In some embodiments, the communications interface 78 can include any suitable hardware, software, or combination of hardware and software that is capable of coupling the system 30 to one or more networks and/or additional devices. The communications interface 78 can be arranged to operate with any suitable technique for controlling information signals using a desired set of communications protocols, services or operating procedures. The communications interface 78 can include the appropriate physical connectors to connect with a corresponding communications medium, whether wired or wireless.

Vehicles of communication comprise a network. In various aspects, the network can include local area networks (LAN) as well as wide area networks (WAN) including without limitation Internet, wired channels, wireless channels, communication devices including telephones, computers, wire, radio, optical or other electromagnetic channels, and combinations thereof, including other devices and/or components capable of/associated with communicating data. For example, the communication environments comprise in-body communications, various devices, and various modes of communications such as wireless communications, wired communications, and combinations of the same.

Wireless communication modes comprise any mode of communication between points (e.g., nodes) that utilize, at least in part, wireless technology including various protocols and combinations of protocols associated with wireless transmission, data, and devices. The points comprise, for example, wireless devices such as wireless headsets, audio and multimedia devices and equipment, such as audio players and multimedia players, telephones, including mobile telephones and cordless telephones, and computers and computer-related devices and components, such as printers, network-connected machinery, and/or any other suitable device or third-party device.

Wired communication modes comprise any mode of communication between points that utilize wired technology including various protocols and combinations of protocols associated with wired transmission, data, and devices. The points comprise, for example, devices such as audio and multimedia devices and equipment, such as audio players and multimedia players, telephones, including mobile telephones and cordless telephones, and computers and computer-related devices and components, such as printers, network-connected machinery, and/or any other suitable device or third-party device. In various implementations, the wired communication modules can communicate in accordance with a number of wired protocols. Examples of wired protocols can include Universal Serial Bus (USB) communication, RS-232, RS-422, RS-423, RS-485 serial protocols, FireWire, Ethernet, Fibre Channel, MIDI, ATA, Serial ATA, PCI Express, T-1 (and variants), Industry Standard Architecture (ISA) parallel communication, Small Computer System Interface (SCSI) communication, or Peripheral Component Interconnect (PCI) communication, to name only a few examples.

Accordingly, in various aspects, the communications interface 78 can include one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the communications interface 78 can include a wireless interface comprising one or more antennas, transmitters, receivers, transceivers, amplifiers, filters, control logic, and so forth.

In various aspects, the communications interface 78 can provide data communications functionality in accordance with a number of protocols. Examples of protocols can include various wireless local area network (WLAN) protocols, including the Institute of Electrical and Electronics Engineers (IEEE) 802.xx series of protocols, such as IEEE 802.11a/b/g/n/ac, IEEE 802.16, IEEE 802.20, and so forth. Other examples of wireless protocols can include various wireless wide area network (WWAN) protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols can include wireless personal area network (PAN) protocols, such as an Infrared protocol, a protocol from the Bluetooth Special Interest Group (SIG) series of protocols (e.g., Bluetooth Specification versions 5.0, 6, 7, legacy Bluetooth protocols, etc.) as well as one or more Bluetooth Profiles, and so forth. Yet another example of wireless protocols can include near-field communication techniques and protocols, such as electro-magnetic induction (EMI) techniques. An example of EMI techniques can include passive or active radio-frequency identification (RFID) protocols and devices. Other suitable protocols can include Ultra Wide Band (UWB), Digital Office (DO), Digital Home, Trusted Platform Module (TPM), ZigBee, and so forth.

In some embodiments, at least one non-transitory computer-readable storage medium is provided having computer-executable instructions embodied thereon, wherein, when executed by at least one processor, the computer-executable instructions cause the at least one processor to perform embodiments of the methods described herein. This computer-readable storage medium can be embodied in memory subsystem 76.

In some embodiments, the memory subsystem 76 can include any machine-readable or computer-readable media capable of storing data, including both volatile/non-volatile memory and removable/non-removable memory. The memory subsystem 76 can include at least one non-volatile memory unit. The non-volatile memory unit is capable of storing one or more software programs. The software programs can contain, for example, applications, user data, device data, and/or configuration data, or combinations therefore, to name only a few. The software programs can contain instructions executable by the various components of the system 30.

In various aspects, the memory subsystem 76 can include any machine-readable or computer-readable media capable of storing data, including both volatile/non-volatile memory and removable/non-removable memory. For example, memory can include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

In one embodiment, the memory subsystem 76 can contain an instruction set, in the form of a file for executing various methods, such as methods including dynamic PET imaging using a trained neural network, as described herein. The instruction set can be stored in any acceptable form of machine readable instructions, including source code or various appropriate programming languages. Some examples of programming languages that can be used to store the instruction set comprise, but are not limited to: Java, C, C++, C#, Python, Objective-C, Visual Basic, or .NET programming. In some embodiments a compiler or interpreter is comprised to convert the instruction set into machine executable code for execution by the processing subsystem 72.

Each functional component described herein can be implemented in computer hardware, in program code, and/or in one or more computing systems executing such program code as is known in the art. As discussed above with respect to FIGS. 1 and 12, such a computing system can include one or more processing units which execute processor-executable program code stored in a memory system. Similarly, each of the disclosed methods and other processes described herein can be executed using any suitable combination of hardware and software. Software program code embodying these processes can be stored by any non-transitory tangible medium, as discussed above with respect to FIGS. 1 and 12.

Although the subject matter has been described in terms of exemplary embodiments, it is not limited thereto. Rather, the appended claims should be construed broadly, to include other variants and embodiments, which can be made by those skilled in the art.

What is claimed is:
1. A system, comprising:
a positron emission tomography (PET) imaging modality configured to acquire a PET dataset;
a magnetic resonance imaging (MRI) modality configured to acquire an MRI dataset; and
a processor configured to:
receive the PET dataset and the MRI dataset;
generate an MRI reconstructed image from the MRI dataset, wherein the MRI reconstructed image is registered to the PET dataset;
apply an iterative reconstruction process to the PET dataset and the MRI reconstructed image, wherein the iterative reconstruction process includes one or more similarity coefficients;
calculate an adaptive hyperparameter for each iteration of the iterative reconstruction process; and
output a reconstructed image from the iterative reconstruction process, wherein iterative reconstruction process comprises an optimization algorithm and a potential function,
wherein: (1) the optimization algorithm comprises a one-step-late (OSL) algorithm defined as:

$$u_j^{n+1} = \frac{u_j^n}{\sum_{i=1}^M g_{ij}n_i a_i - \beta \frac{\partial R(u^n)}{\partial u_j}} \sum_{i=1}^M g_{ij}n_i a_i \frac{y_i}{n_i a_i \sum_b g_{ib} u_b^n + r_i}$$

where i is a line-of-response (LOR) index, M is a number of LORs, $r_i$ is scatter and random coincidences, $n_i$ is a normalization, $\alpha_i$ is attenuation factors, $g_{ij}$ is a system matrix, $\beta$ is the adaptive hyperparameter, u is a measured activity distribution, R(u) is the potential function, and i is a voxel index; or
(2) the optimization algorithm comprises a preconditioned gradient ascent (PGA) algorithm defined as:

$$u_j^{n+1} = \frac{u_j^n}{\sum_{i=1}^M g_{ij}n_i a_i} \sum_{i=1}^M g_{ij}n_i a_i \frac{y_i}{n_i a_i \sum_b g_{ib} u_b^n + r_i} + \beta \frac{\partial R(u^n)}{\partial u_j}$$

where i is a line-of-response (LOR) index, M is a number of LORs, $r_i$ is scatter and random coincidences, $n_i$ is a normalization, $\alpha_i$ is attenuation factors, $g_{ij}$ is a system matrix, $\beta$ is the adaptive hyperparameter, u is a measured activity distribution, R(u) is the potential function, and j is a voxel index; or
(3) the optimization algorithm comprises a penalized likelihood based on a separable surrogate (PLSS) algorithm defined as:

$$u_j^{n+1} = \frac{2u_{j,EM}^{n+1}}{(1 - \beta u_{j,reg}^{n+1}) + \sqrt{(1 - \beta u_{j,reg}^{n+1})^2 + 4\beta u_{j,reg}^{n+1}}}$$

where $\beta$ is the adaptive hyperparameter, u is a measured activity distribution, and $u_{j,EM}^{n+1}$ is the expectation-maximization estimate of $u_j^n$ smoothed according to:

$$u_{j,reg}^{n+1} = \frac{1}{2\sum_{b \in N_j} \omega_{jb}} \sum_{b \in N_j} \omega_{jb}(u_{j,EM}^n + u_{b,EM}^n)$$

Where b is the index for voxels in a neighborhood $N_j$ and $\omega$ is a similarity coefficient.

2. The system of claim 1, wherein the potential function is selected from the group consisting of quadratic difference (PFQ) function or a relative difference (RD) function.

3. The system of claim 1, wherein the MRI dataset is obtained at least partially simultaneously with the PET dataset; or the MRI dataset is obtained sequentially with the PET dataset.

4. A system, comprising:
   a positron emission tomography (PET) imaging modality configured to acquire a PET dataset;
   a magnetic resonance imaging (MRI) modality configured to acquire an MRI dataset; and
   a processor configured to:
      receive the PET dataset and the MRI dataset;
      generate an MRI reconstructed image from the MRI dataset, wherein the MRI reconstructed image is registered to the PET dataset;
      apply an iterative reconstruction process to the PET dataset and the MRI reconstructed image, wherein the iterative reconstruction process includes one or more similarity coefficients;
      calculate an adaptive hyperparameter for each iteration of the iterative reconstruction process; and
      output a reconstructed image from the iterative reconstruction process, wherein the adaptive hyperparameter is generated according to:

$$\beta_j = \alpha \sqrt{u_j \sum_{i=1}^{M} y_{ij} n_i a_i}$$

where $\alpha$ is a constant, u is a measured activity distribution, j is a voxel index, i is a line-of-response (LOR) index, M is the number of LORs, $n_i$ is a normalization, and $\alpha_i$ is attenuation factors.

5. The system of claim 4, wherein the MRI dataset is obtained at least partially simultaneously with the PET dataset; or the MRI dataset is obtained sequentially with the PET dataset.

6. A method of generating a reconstructed clinical image, comprising:
   obtaining a PET dataset;
   obtaining an MRI dataset, where the MRI dataset is registered to the PET dataset;
   generating an MRI reconstructed image from the MRI dataset, wherein the MRI reconstructed image is registered to the PET dataset;
   applying an iterative reconstruction process based on the PET dataset and the MRI reconstructed image, wherein the iterative reconstruction process includes one or more similarity coefficients;
   calculating a spatially variant adaptive hyperparameter for each iteration of the iterative reconstruction process; and
outputting a reconstructed image from the iterative reconstruction process, wherein the iterative reconstruction process comprises an optimization algorithm and a potential function,
   wherein: (1) the optimization algorithm comprises an one-step-late (OSL) algorithm defined as:

$$u_j^{n+1} = \frac{u_j^n}{\sum_{i=1}^{M} g_{ij} n_i a_i - \beta \frac{\partial R(u^n)}{\partial u_j}} \sum_{i=1}^{M} g_{ij} n_i a_i \frac{y_i}{n_i a_i \sum_b g_{ib} u_b^n + r_i}$$

where i is a line-of-response (LOR) index, M is a number of LORs, $r_i$ is scatter and random coincidences, $n_i$ is a normalization, $\alpha_i$ is attenuation factors, $g_{ij}$ is a system matrix, $\beta$ is the adaptive hyperparameter, u is a measured activity distribution, R(u) is the potential function, and j is a voxel index; or the optimization algorithm comprises a preconditioned gradient ascent (PGA) algorithm defined as:

$$u_j^{n+1} = \frac{u_j^n}{\sum_{i=1}^{M} g_{ij} n_i a_i} \sum_{i=1}^{M} g_{ij} n_i a_i \frac{y_i}{n_i a_i \sum_b g_{ib} u_b^n + r_i} + \beta \frac{\partial R(u^n)}{\partial u_j}$$

where i is a line-of-response (LOR) index, M is a number of LORs, $r_i$ is scatter and random coincidences, $n_i$ is a normalization, $\alpha_i$ is attenuation factors, $g_{ij}$ is a system matrix, $\beta$ is the adaptive hyperparameter, u is a measured activity distribution, R(u) is the potential function, and j is a voxel index; or the optimization algorithm comprises a penalized likelihood based on a separable surrogate (PLSS) algorithm defined as:

$$u_j^{n+1} = \frac{2 u_{j,EM}^{n+1}}{\left(1 - \beta u_{j,reg}^{n+1}\right) + \sqrt{\left(1 - \beta u_{j,reg}^{n+1}\right)^2 + 4\beta u_{j,reg}^{n+1}}}$$

where $\beta$ is the adaptive hyperparameter, u is a measured activity distribution, and $u_{j,EM}^{n+1}$ is the expectation-maximization estimate of $u_j^n$ smoothed according to:

$$u_{j,reg}^{n+1} = \frac{1}{2 \sum_{b \in N_j} \omega_{jb}} \sum_{b \in N_j} \omega_{jb} \left(u_{j,EM}^n + u_{b,EM}^n\right)$$

where b is the index for voxels in a neighborhood $N_j$ and $\omega$ is a similarity coefficient.

7. The method of claim 6, wherein the potential function is selected from the group consisting of quadratic difference (PFQ) function or a relative difference (RD) function.

8. The method of claim 6, wherein the MRI dataset is obtained at least partially simultaneously with the PET dataset; or the MRI dataset is obtained sequentially with the PET dataset.

9. A method of generating a reconstructed clinical image, comprising:
   obtaining a PET dataset;
   obtaining an MRI dataset, where the MRI dataset is registered to the PET dataset;
   generating an MRI reconstructed image from the MRI dataset, wherein the MRI reconstructed image is registered to the PET dataset;
   applying an iterative reconstruction process based on the PET dataset and the MRI reconstructed image, wherein the iterative reconstruction process includes one or more similarity coefficients;

calculating a spatially variant adaptive hyperparameter for each iteration of the iterative reconstruction process; and outputting a reconstructed image from the iterative reconstruction process, wherein the adaptive hyperparameter is generated according to:

$$\beta_j = \alpha \sqrt{u_j \sum_{i=1}^{M} y_{ij} n_i a_i}$$

where $\alpha$ is a constant, u is a measured activity distribution, j is a voxel index, i is a line-of-response (LOR) index, M is the number of LORs, $n_i$ is a normalization, and $\alpha_i$ is attenuation factors.

10. The method of claim 9, wherein the MRI dataset is obtained at least partially simultaneously with the PET dataset; or the MRI dataset is obtained sequentially with the PET dataset.

11. A method of generating a reconstructed clinical image, comprising:
obtaining a PET dataset;
obtaining an MRI dataset;
generating an MRI reconstructed image from the MRI dataset, wherein the MRI reconstructed image is registered to the PET dataset;
applying an iterative reconstruction process based on the PET dataset and the MRI reconstructed image, wherein the iterative reconstruction process comprises an optimization algorithm and a potential function;
calculating an adaptive hyperparameter for each iteration of the iterative reconstruction process; and
outputting a reconstructed image from the iterative reconstruction process, wherein the adaptive hyperparameter is generated according to:

$$\beta_j = \alpha \sqrt{u_j \sum_{i=1}^{M} y_{ij} n_i a_i}$$

where $\alpha$ is a constant, u is a measured activity distribution, j is a voxel index, i is a line-of-response (LOR) index, M is the number of LORs, $n_i$ is a normalization, and $\alpha_i$ is attenuation factors.

* * * * *